US006878338B2

(12) United States Patent  
Taylor et al.

(10) Patent No.: US 6,878,338 B2  
(45) Date of Patent: Apr. 12, 2005

(54) DUAL CHAMBER DISSOLUTION CONTAINER WITH PASSIVE AGITATION

(75) Inventors: Michael A. Taylor, Napa, CA (US); Carolyn Fitzgerald, Napa, CA (US)

(73) Assignee: Prismedical Corporation, Napa, CA (US)

( * ) Notice: Subject to any disclaimer, the term of this patent is extended or adjusted under 35 U.S.C. 154(b) by 129 days.

(21) Appl. No.: 10/141,501

(22) Filed: May 6, 2002

(65) Prior Publication Data

US 2003/0012690 A1 Jan. 16, 2003

Related U.S. Application Data

(60) Provisional application No. 60/289,030, filed on May 4, 2001.

(51) Int. Cl.[7] .................................................. B01L 3/00
(52) U.S. Cl. ........................ 422/61; 422/100; 422/102; 604/82; 604/85; 604/87; 604/92
(58) Field of Search .......................... 422/61, 100, 102; 366/336, 340; 604/82, 85, 87, 92

(56) References Cited

U.S. PATENT DOCUMENTS

| | | | |
|---|---|---|---|
| 3,276,458 A | 10/1966 | Iversen et al. | |
| 3,517,816 A | 6/1970 | Hoppen | |
| 3,715,189 A | 2/1973 | Nighohossian et al. | |
| 3,730,349 A | 5/1973 | Hermann | |
| 3,739,947 A | 6/1973 | Baumann et al. | |
| 4,070,289 A | 1/1978 | Akcasu | |
| 4,160,727 A | 7/1979 | Harris, Jr. | |
| 4,231,872 A | 11/1980 | Keil | |
| 4,280,912 A | 7/1981 | Berry, III et al. | |
| 4,396,383 A | 8/1983 | Hart | |
| 4,458,733 A | 7/1984 | Lyons | |
| 4,484,920 A | 11/1984 | Kaufman | |
| 4,507,114 A | 3/1985 | Bohman et al. | |
| 4,511,351 A | 4/1985 | Theeuwes | |
| 4,533,348 A | 8/1985 | Wolfe et al. | |
| 4,534,757 A | 8/1985 | Geller | |
| 4,576,603 A | 3/1986 | Moss | |
| 4,648,978 A | 3/1987 | Makinen et al. | |
| 4,695,272 A | 9/1987 | Berglund et al. | |
| 4,698,153 A | 10/1987 | Matsuzaki et al. | |
| 4,784,763 A | 11/1988 | Hambleton et al. | |
| 4,810,388 A | 3/1989 | Trasen | |
| 4,871,463 A | 10/1989 | Taylor et al. | |
| 4,874,366 A | 10/1989 | Zdeb et al. | |
| 4,903,717 A | 2/1990 | Sumnitsch | |
| 4,994,056 A | 2/1991 | Ikeda | |
| 5,004,535 A | 4/1991 | Bosko et al. | |
| 5,032,265 A | 7/1991 | Jha et al. | |
| 5,059,317 A | 10/1991 | Marius et al. | |
| 5,163,922 A | 11/1992 | McElveen, Jr. et al. | |
| 5,201,705 A | 4/1993 | Berglund et al. | |
| 5,259,954 A | 11/1993 | Taylor | |
| 5,395,323 A | 3/1995 | Berglund | |
| 5,429,603 A | 7/1995 | Morris | |
| 5,514,090 A | 5/1996 | Kriesel et al. | |
| 5,531,683 A | 7/1996 | Kriesel et al. | |

(Continued)

FOREIGN PATENT DOCUMENTS

WO  WO 00 66214 A  11/2000

OTHER PUBLICATIONS

International Search Report re International Appln. No. PCT/US02/14576, Date of mailing of ISR: Nov. 5, 2002.

Primary Examiner—Jan M. Ludlow
(74) Attorney, Agent, or Firm—Knobbe, Martens, Olsen & Bear LLP

(57) ABSTRACT

A reagent dissolution device and methods of using the same, wherein the device comprises a housing (40), a diluent (25), and at least one reagent bed (35), wherein the diluent (25) and the at least one reagent bed (35) are separated by a friable barrier (50) and a flow distribution disk (100). Alternate embodiments include chambers with a plurality of reagent beds as well as chambers for the mixing of two or more liquid reagents.

23 Claims, 5 Drawing Sheets

U.S. PATENT DOCUMENTS

| | | |
|---|---|---|
| 5,578,005 A | 11/1996 | Sancoff et al. |
| 5,637,087 A | 6/1997 | O'Neil et al. |
| 5,685,846 A | 11/1997 | Michaels, Jr. |
| 5,725,777 A | 3/1998 | Taylor |
| 5,752,940 A | 5/1998 | Grimard |
| 5,785,682 A | 7/1998 | Grabenkort |
| 5,807,323 A | 9/1998 | Kriesel et al. |
| 6,274,103 B1 | 8/2001 | Taylor |
| 6,428,505 B1 | 8/2002 | Taylor |

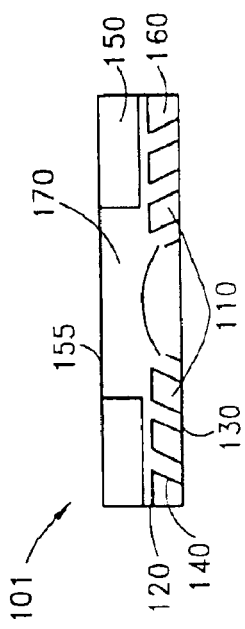
FIG. 2A
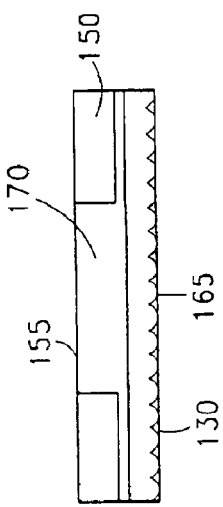
FIG. 2B
FIG. 2C
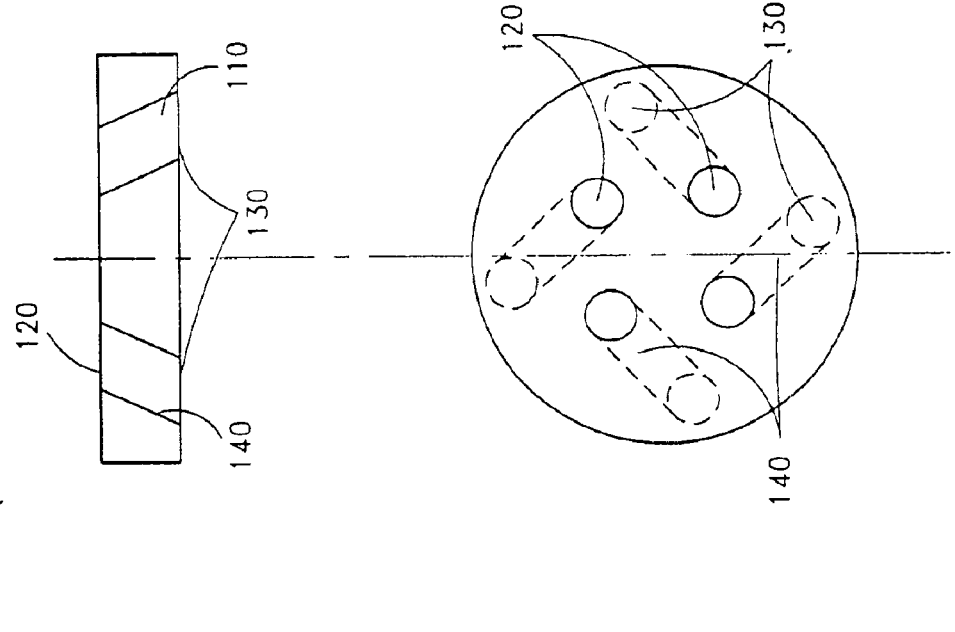

DUAL CHAMBER DISSOLUTION CONTAINER WITH PASSIVE AGITATION

RELATED APPLICATIONS

This application claims priority to U.S. Provisional Patent Application 60/289,030, filed May 4, 2001, the disclosure of which is incorporated by reference in its entirety.

BACKGROUND OF THE INVENTION

Numerous combinations of reagents that have beneficial or desirable characteristics can lose their desirable properties over time. This transition can be prevented by maintaining each component separately prior to use, e.g., until their combined function is desired. Examples of these combinations include reagent aggregation in solution, reagent degradation, production of gases that alter the concentration or physical properties of the solution, and changes in pH, color, taste of regent in solution.

An additional problem associated with combining dry and wet reagents within a closed housing is the difficulty in ensuring that the reagents are completely dissolved. Manipulation is usually required to ensure that the dry reagent is exposed to the diluent. The potential for incomplete dissolution is increased by the need for agitation. The duration and degree of agitation is directly proportional to the degree of dry reagent dissolution. Without adequate agitation, dry reagents may not be completely dissolved and the resulting solution would have the desired characteristics.

The difficulty associated with achieving complete dissolution of reagent is more difficult when a small volume of diluent is used to dissolve a large volume amount of dry reagent. The preparation of certain solutions is particularly difficult with combinations that use small volumes of diluent compared to the dry reagent volume. Examples of these types of combinations include vaccines, biotechnology derived drugs and concentrates of any form. This problem is also difficult with poorly soluble reagents.

With some combinations of reagents, excessive agitation produces undesirable characteristics. For example, protein-containing solutions produce foaming with excessive agitation. Foaming of protein solutions can lead to protein denaturation, which can destroy the activity of the protein solution. Additionally, foaming can prevent complete delivery of the solution from the preparation container as some portion of the foam will frequently remain in the vessel used for agitation.

Methods used to combine wet and dry reagents include containment of reagents in separate containers that are joined together, then the separation is removed and the reagents are combined by vigorous agitation of the combined containers. Other attempts to prepare a solution from separated components include containment of the components separately within a single packaging. These include containment of diluent within a bag that has a breakable barrier or perforation mechanism that allows contact of the separated reagents.

For these and other reasons, apparatus and methods for dissolving and mixing reagents rapidly, efficiently, and with minimal agitation would be desirable.

DESCRIPTION OF THE DRAWINGS

FIG. 2 shows multiple embodiments of a flow distribution disk. FIG. 2A shows a cross section and a top-down view of one flow distribution disk embodiment for use with the mechanism of FIG. 1. FIG. 2B shows a cross section of an alternate flow distribution disk embodiment. FIG. 2C shows a cross section of another alternate flow distribution disk embodiment.

FIG. 3 shows a plunger-driven reagent dissolution chamber.

FIG. 4 shows a spring-driven reagent dissolution chamber.

FIG. 5 shows a spring-driven reagent dissolution chamber containing a first liquid reagent and a second liquid reagent.

DETAILED DESCRIPTION OF THE PREFERRED EMBODIMENTS

The desirable effects of mixture of dry reagents dissolved in diluent may be diminished over time. Similarly, the mixture of some wet reagent combinations may produce undesirable results if the mixture is allowed to stand for extended periods of time. To mitigate this possibility, this description below provides apparatuses and methods of using same that maintain desired reagents separately until mixing is needed. This is accomplished within a closed housing. Production of pressure within the housing induces rupture of a friable barrier exposing one reagent to the diluent. Increased efficiency of dissolution of dry reagents or mixing of fluid reagents is achieved due to generation of directional flow within the reagent bed due to flow directing channels with a flow directing disk. The passively induced agitation creates vortices within the closed housing.

Figure 1:
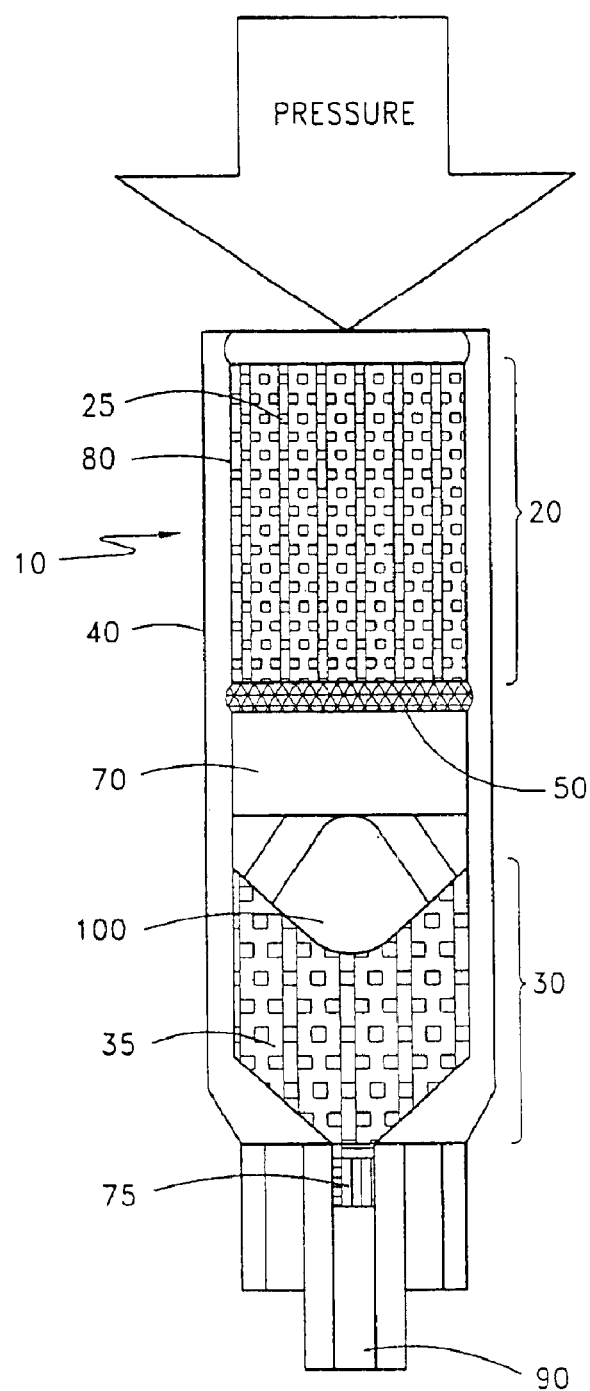
FIG. 1 shows a cross section view of a generic reagent dissolution chamber in accordance with the preferred embodiments.

A reagent dissolution chamber is shown in FIG. 1. The embodiment depicted in FIG. 1 shows a reagent dissolution chamber 10 comprising a diluent chamber 20 with a diluent 25 and at least one reagent chamber 30 with a reagent 35 within a housing 40. The diluent chamber and the at least one reagent chamber are separated by a friable barrier 50. Note that in the other arrangements, diluent can be provided separately as disclosed in U.S. Pat. No. 6,274,103, issued Aug. 14, 2001, the disclosure of which is hereby incorporated by reference in its entirety. The friable barrier enables formation of a dual chamber for separate containment of dry reagent and diluent/therapeutic fluid. This is advantageous for any combination of materials that, when in contact, induce a deleterious effect over time. This deleterious effect could include formation of precipitation or crystals, loss of efficacy or formation of gases. Examples of combinations of reagents include therapeutic agents and diluents, multi-component cleaning solutions and sterilizing solutions. Examples of these are an antibiotic and the diluent (Cefazolin and Saline), combination anti-nerve gas agents (Hl-6 and Atropine), or peracetic acid prepared from a combination of reagents.

A flow distribution disk 100 is located within a housing 40 between the diluent chamber 20 and the at least one reagent chamber 30. The flow distribution disk 100 generates a distribution of diluent flow within a closed housing. The compound angles between the inlet and outlet ports of the disk create a flow directed from the central portion of the housing 40 toward the periphery. The result is generation of passive agitation at the periphery of the housing interior. This flushing effect due to the spiraled flow within the reagent bed 35 increases the efficiency of dissolution.

For example, as the diluent is forced through the dry reagent bed 35, the reagent or reagents in the bed are dissolved and reduced in volume. As this occurs, a compressed porous expansion component 70 expands, moving the flow distribution disk 100 axially within the housing to maintain contact with the reagent bed 35. As the flow distribution disk 100 moves axially, the micro-spirals or vortexes of diluent progress axially until the reagent bed is dissolved and the flow distribution disk 100 is in contact with the terminal portion of the housing. As depicted in FIG. 1, the shape of the flow distribution disk 100 is preferably adapted to permit a flush interaction of the disk with the housing 40.

Another embodiment includes incorporation of external grooves on the interior of the housing with corresponding projections from the flow distribution disk. The grooves can be vertical within the housing or spiral. Vertical grooves would provide uniform axial movement of the flow distribution disk perpendicular to the housing. Grooves in a spiral pattern would provide uniform rotation of the flow distribution disk as it moves down the length of the housing. Both of these embodiments provide a uniform and complete exposure of the diluent to the entire housing interior and the dry reagent bed. Alternately, the grooves can be located in the flow distribution disk with corresponding projections from the housing interior.

An embodiment of a flow distribution disk is shown in FIGS. 2A–C. The embodiments depicted in FIG. 2 shows a flow distribution disk 100 comprising a plurality of directional channels 110. A directional channel comprises an inlet port 120 and an outlet port 130 connected by a flow channel 140.

The inlet and outlet ports connected by directional channels are arranged in the flow distribution disk 100 at compound angles to direct diluent passing through the flow distribution disk into the reagent bed. Picturing the flow distribution disk 100 in a three-dimensional system where X is the horizontal axis, Y is the lateral axis and Z is the vertical axis. From the horizontal axis, typical angles are between 30 and 90 degrees, preferably between 45 and 75 degrees and more preferably between 55 and 65 degrees. In the same system the Y angles would be between 30 and 90, preferably between 45 and 75 degrees and more preferably between 55 and 65 degrees. In the same system the Z angles would be between 30 and 90, preferably between 45 and 75 degrees and more preferably between 55 and 65 degrees. In practice, when pressure is applied to the diluent chamber, diluent flows to the flow distribution disk 100 and the inlet ports 120. Diluent passes through the inlet ports and enters the directional channels in the flow distribution disk. The diluent then passes through the outlet ports.

The flow distribution disk embodiment shown in FIG. 2A has a plurality of directional channels 110 disposed at approximately 30 degrees sloping away from the center of the flow distribution disk. Although four directional channels are depicted in the lower part of the figure, additional channels can be included in the disk. When diluent passes through the flow distribution disk, the flow creates multiple spiral flows within the reagent bed. The directional channels can have progressively diminished diameter from the inlet to the outlet ports to create a venturi effect. The result of such an embodiment would be to enhance diluent flow rate from the outlet ports. Alternatively, the directional channels can have dual conical pores with constrictions in the center of the flow distribution disk.

In another embodiment, the directional channels can connect laterally to ports on the peripheral sides of the flow distribution disk. In such an embodiment, diluent forced through the flow distribution disk is directed toward the interior housing wall or at the very peripheral end of the downstream edge of the flow distribution disk. The former ensures that the interior housing wall is flushed by the diluent. The latter ensures that agitation is focused at the peripheral margins of the housing interior.

The flow distribution disk embodiment shown in FIG. 2B also has a plurality of directional channels 110 disposed at approximately 30 degrees sloping away from the center of the flow distribution disk. In this embodiment, the flow distribution disk comprises two layers, a top layer 150 and a bottom layer 160 that, when placed adjacent to each other form a distribution chamber 170. In the depicted embodiment, the top layer has a central pore 155 through which the diluent flows when the device is in use. The top layer directs the diluent from the diluent chamber to the central pore. The diluent then passes through the central pore to the inlet ports 120, the flow channels 140 and the outlet ports 130 that make up the directional channels 110.

The flow distribution disk embodiment shown in FIG. 2C comprises a top layer 150 and a porous plate 165. The porous plate can be composed of hydrophobic materials to hinder flow of hydrophilic materials, which is designed to aid in spreading the diluent flow across the face reagent bed. The outlet of the porous plate 165 comprises a plurality of outlet ports 130.

From the discussion above it is apparent that a pressure generating structure facilitates the function of the disclosed device. In the embodiment shown in FIG. 3, a plunger is used to push the diluent through the device. Alternative embodiments include the use of molded or metal springs. Various embodiments are discussed below.

Figure 3A:
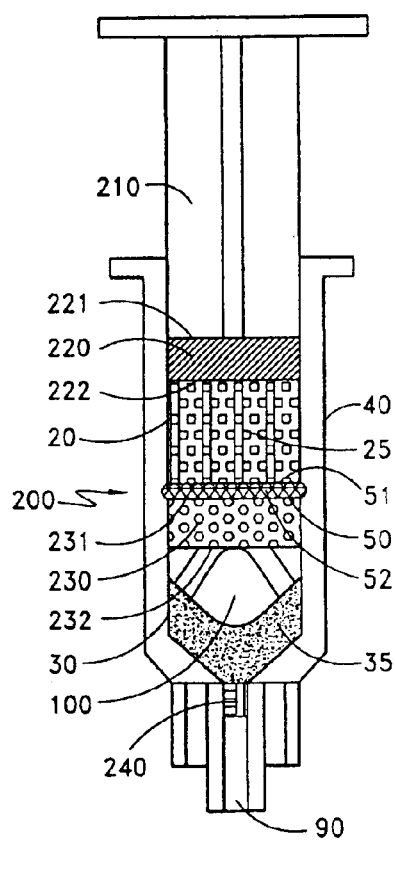
FIG. 3A shows the chamber in a fully loaded, ready-to-use state.
Figure 3B:
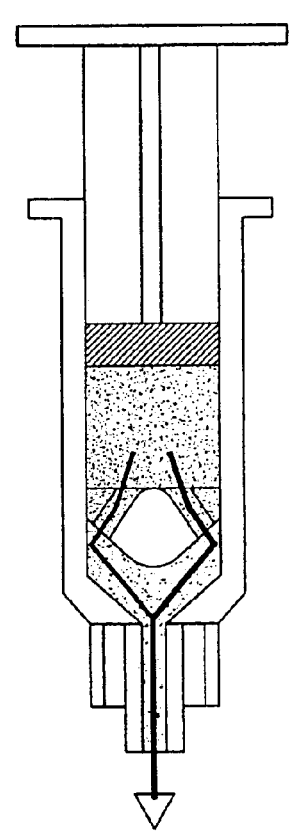
FIG. 3B shows the chamber in a partially depressed state with the dark arrow indicating diluent flow through the flow distribution disk and through the reagent chamber.
Figure 3C:
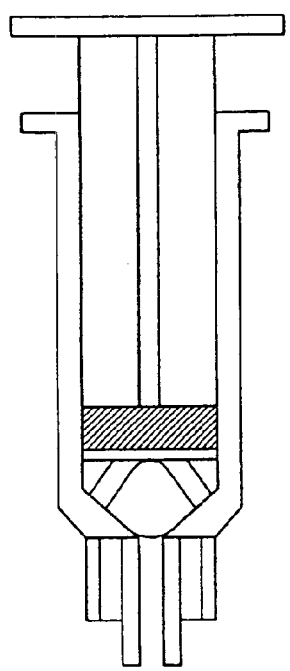
FIG. 3C shows a discharged chamber.

A plunger driven reagent dissolution device 200 is shown in FIG. 3. The device comprises a housing 40, which includes a diluent chamber 20 and at least one reagent chamber 30 separated by a friable barrier 50. The housing also includes a housing outlet 90. A diluent 25 is located in the diluent chamber 20. One or more reagents of interest 35 are located in the at least one reagent chamber 30. A flow distribution disk 100 is located between the diluent chamber 20 and the reagent chamber 30.

A plunger 210 is located adjacent to the diluent chamber 20. The diluent is contained within the diluent chamber 20 formed by a plug seal 220, the housing 40 and the friable barrier 50. The plug seal comprises a pressure generating side 201 and a diluent side 222. The plug seal 220 is typically composed of a non-porous, elastic material that conforms to the interior walls of the housing 40, forming a seal between the plug seal and the housing walls. The friable barrier 50 is comprised of a diluent side 51 and a reagent bed side 52, and is typically composed of a non-porous, non-elastic material. The friable barrier 50 bursts when a differential pressure occurs on one side of the barrier 50. This pressure is between 5 and 90 pounds per square inch (PSI), preferably 10 and 75 PSI and more preferably between 20 and 30 PSI. In the depicted embodiment, the plunger 210 generates pressure within the chamber 20 by transferring pressure from the plunger 210 to the pressure generating side 225 of the plug 220.

A porous expansion component 230 is located within the chamber adjacent to the reagent bed side 52 of the friable barrier 50. The porous expansion component 230 comprises a diluent side 231 and a reagent bed side 232. The porous expansion component 230 typically consists of a porous, compressible material that has an elastic memory. The porous expansion component 230 is compressed when the device is prepared. When the device is in use, the porous expansion component 230 is induced to expand to its original axial length following release from compression. Suitable materials for use as the component include polyurethane foam, springs such as molded polymeric springs, metal springs, and the like.

Adjacent to the reagent bed side 232 of the porous expansion component 230 is a dry reagent bed 35. One or more discrete reagent beds can be located within the dry reagent bed portion of the device 200. When more than one reagent bed is used, each bed can be separated by an additional friable barrier, a porous barrier that permits diluent to pass through while restraining the dry reagent, or other suitable barrier. Downstream of the dry reagent bed 35 is a reagent bed restraint 240. The reagent bed restraint is typically composed of an inert porous material. One example of a reagent bed restraint 240 is a porous polyethylene plug. The housing outlet 90 is located downstream from the dry reagent bed and reagent bed restraint 240.

In practice, the plunger 210 is depressed from a starting point shown in FIG. 3A, which depicts a fully charged reagent dissolution device 200. As the plunger 210 moves into the diluent chamber 20, pressure is generated against the friable barrier 50 until the barrier is ruptured. Diluent then flows into the porous expandable material 230 and into the flow distribution disk 100. The diluent then leaves the flow distribution disk 100 forming micro-vortexes that facilitate the dissolution of the reagent 35. This flow and mixing is indicated by the dark lines in FIG. 5B, which depicts a partially discharged device 200. The device 200 depicted in FIG. 5C has been fully discharged.

Figure 4A:
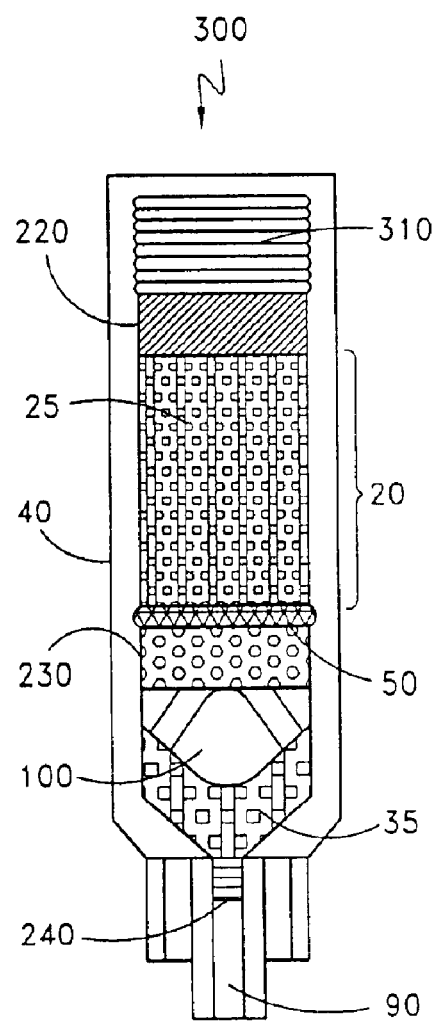
FIG. 4A shows the chamber in a fully loaded, ready-to-use state.
Figure 4B:
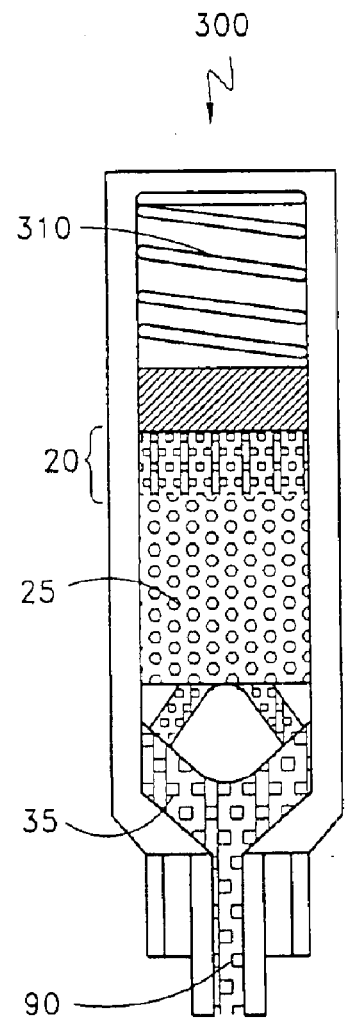
FIG. 4B shows the chamber in a partially depressed state.

A spring driven reagent dissolution device 300 is shown in FIG. 4. In the illustrated embodiment, the housing 40, diluent chamber 20, reagent chamber 30, and other features of the device 300 are the similar to those shown in FIG. 3. The pressure-generating component of this embodiment, however, is not a plunger but an expanding material such as a spring 310. The spring 310 is located adjacent to the pressure generating side of the plug seal 220. Typically the spring 310 or other expandable material is held in a compressed form that can be released to apply pressure to the plug seal 220. After the spring 310 or other expandable material is released and begins to expand, movement of the plug seal 220 into the diluent chamber 20 generates pressure on the diluent 25 that causes the friable barrier 50 to bursts. As the spring expands, it drives the plug seal and the diluent toward porous expansion component 230 and the flow distribution disk 100. The diluent passes through the flow distribution disk 100 dissolving the dry reagent in the reagent bed 35. As the prepared solution emerges from the reagent chamber 30, it can be filtered by the reagent restraint 240. Alternatively, the reagent restraint can be displaced by the flow of solution out of the reagent chamber. Ultimately, the prepared solution flows from the housing outlet port 90.

Another spring driven reagent dissolution device 400 is shown in FIG. 5. In the illustrated embodiment, the housing 40, and other features of the device are the similar to those shown in FIG. 4. However, this reagent dissolution device 400 is designed to mix two liquid reagents, a first liquid reagent 410 and a second liquid reagent 420, rather than a diluent and a dry reagent. Just as with the embodiment shown in FIG. 4, after the spring 310 or other expandable material in the reagent dissolution device 400 is released, resultant movement of the plug seal 220 into the diluent chamber 20 generates pressure that causes the friable barrier 50 to bursts. As the spring 310 expands, it drives the plug seal 220 and the first liquid reagent 410 toward the flow distribution disk 100. The first liquid reagent passes through the flow distribution disk 100 and mixes with the second liquid reagent 420.

In one embodiment, attachment of a hydrophobic barrier to the flow distribution disk can replace the porous expansion component. In this embodiment, after rupture of the friable barrier 50 by the application of pressure, the first liquid reagent 410 is forced through the hydrophobic barrier and through the flow distribution disk 100. The second liquid reagent 420 is then mixed with the first liquid reagent 410 to form the solution of interest. This mixing process is enhanced by the directed flow resulting from the flow distribution disk 100. Such an embodiment can be pressured by a plunger or spring driven pressurization.

Figure 5C:
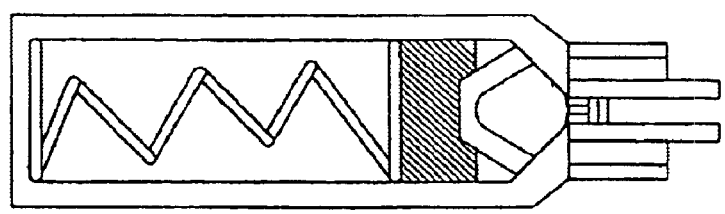
FIG. 5C shows a discharged chamber.
Figure 5B:
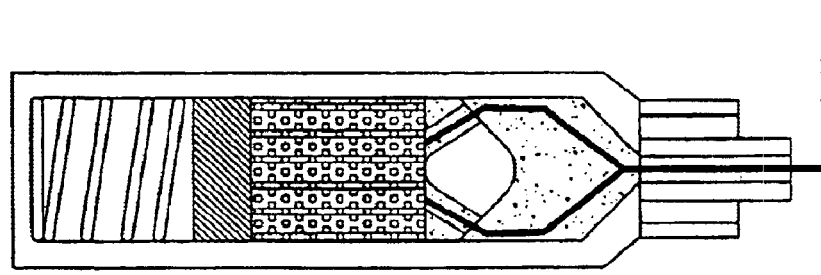
FIG. 5B shows the chamber in a partially depressed state with the dark arrow indicating diluent flow through the flow distribution disk and through the reagent chamber.
Figure 5A:
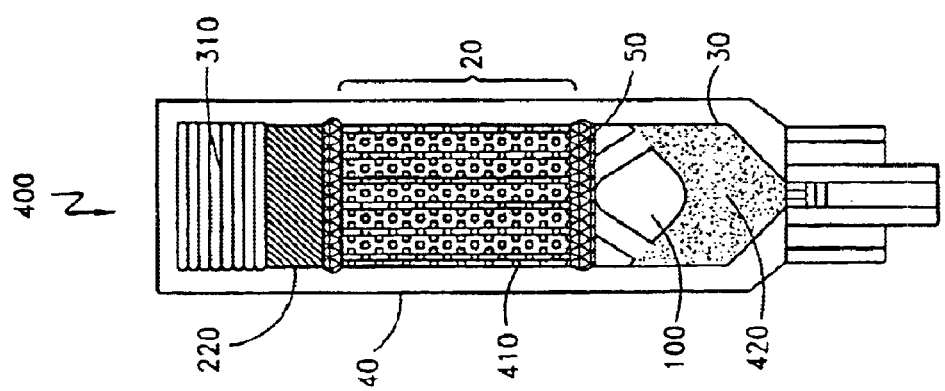
FIG. 5A shows the chamber in a fully loaded, ready-to-use state.

FIG. 5A depicts a fully charged reagent dissolution device, FIG. 5B shows a partially discharged device, and FIG. 5C depicts a fully discharged device.

EXAMPLE

An example of a reagent dissolution device is a device for the preparation of a typical antibiotic solution (e.g., a cephalosporin such as CEFAZOLIN™). The reagent dissolution device comprises a housing with a diluent of pharmaceutical grade water and a reagent bed comprising 1000 mg of a cephalosporin. The reagent dissolution chamber has a plunger, as depicted in FIG. 3.

When the time comes to prepare the antibiotic solution, the user depresses the plunger. Depression of the plunger results in the generation of pressure within the chamber sufficient to burst the friable barrier in the dissolution chamber. Once the friable barrier bursts, diluent flows toward the dry reagent bed containing the cephalosporin. As the diluent flow passes through the flow distribution disk, the force of the flow is directed from the central area of the flow distribution disk to the periphery. Additionally, the constriction of flow produced by the reduction in flow channels in the flow distribution disk induces an augmentation in flow velocity. The resulting effect is the generation of micro-spirals or vortices at the periphery of the interior of the housing at the upstream surface of the dry reagent bed. These micro-spirals enhance the dissolution rate of a dry reagent bed by creating passive dissolution requiring no external agitation or mixing. The net result is bolus delivery of an antibiotic solution.

Although the invention has been described with reference to embodiments and examples, it should be understood that various modifications can be made without departing from the spirit of the invention. Accordingly, the invention is limited only by the following claims.

What is claimed is:

1. A reagent delivery device comprising:

a housing defining a fluid flow path therethrough, at least one reagent bed within the housing;

a compression component exerting pressure upon the at least one reagent bed; and a flow distribution disk positioned upstream of the at least one reagent bed, the disk including at least one angled flow passage therethrough, wherein the at least one angled flow passage is disposed at an angle that is disposed at a range of 30 to 75 degrees with respect to either a vertical axis or a horizontal axis of the disk.

2. The reagent dissolution device of claim 1, wherein the compression component is porous and expandable and positioned within the housing and upstream of the flow distribution disk.

3. The reagent dissolution device of claim 1, wherein the flow distribution disk comprises a top layer and an adjacently disposed bottom layer that form a distribution chamber.

4. The reagent dissolution device of claim 3, wherein the bottom layer is a porous plate.

5. The reagent dissolution device of claim 3, wherein the at least one angled flow passage is located in the bottom layer and comprises a plurality of directional channels bounded by an inlet port and an outlet port.

6. The reagent dissolution device of claim 1, further comprising a pressure-generating plunger.

7. The reagent dissolution device of claim 1, further comprising a pressure-generating spring.

8. The reagent dissolution device of claim 1, further comprising a diluent.

9. The reagent dissolution device of claim 8, wherein the diluent comprises a first liquid reagent.

10. The reagent dissolution device of claim 9, wherein the at least one reagent bed contains a second liquid reagent.

11. The reagent dissolution device of claim 1, wherein the at least one reagent bed comprises a dry reagent bed.

12. The reagent dissolution device of claim 1, wherein the flow distribution disk is slidably disposed within the housing between the compression component and the at least one reagent bed.

13. A reagent delivery device comprising:
a housing defining a fluid path therethrough;
a dry reagent bed within the housing;
a compression component exerting pressure on the dry reagent bed; and
a flow distribution disk positioned upstream of the dry reagent bed, the disk including at least one angled flow passage therethrough, wherein the at least one angled flow passage comprises a plurality of directional channels disposed at a range from 45 to 75 degrees with respect to a vertical axis of the disk.

14. The reagent delivery device of claim 13, wherein the plurality of directional channels are disposed at a range from 55 to 65 degrees with respect to the vertical axis of the disk.

15. A reagent delivery device, comprising:
a housing defining a fluid flow path therethrough;
at least one reagent bed within the housing; and
a flow distribution disk positioned upstream of the at least one reagent bed, the disk including at least one flow passage therethrough, the flow passage being angled between 45 and 75 degrees with respect to a vertical axis of the disk.

16. The reagent delivery device of claim 15, further comprising a porous expansion component upstream of the flow distribution disk.

17. The reagent delivery device of claim 15, wherein the flow distribution disk is slidably disposed within the housing between the compression component and the at least one reagent bed.

18. The reagent delivery device of claim 15, further comprising a pressure-generating plunger.

19. The reagent delivery device of claim 15, further comprising a pressure-generating spring.

20. The reagent delivery device of claim 15, further comprising a diluent.

21. The reagent delivery device of claim 20, wherein the diluent comprises a first liquid reagent.

22. The reagent delivery device of claim 21, wherein the at least one reagent bed contains a second liquid reagent.

23. The reagent delivery device of claim 15, wherein the at least one reagent bed comprises a dry reagent bed.

* * * * *

UNITED STATES PATENT AND TRADEMARK OFFICE
CERTIFICATE OF CORRECTION

PATENT NO. : 6,878,338 B2 Page 1 of 1
APPLICATION NO. : 10/141501
DATED : April 12, 2005
INVENTOR(S) : Taylor et al.

It is certified that error appears in the above-identified patent and that said Letters Patent is hereby corrected as shown below:

Title Page 1, Col. 2, #74 under "Attorney, Agent, or Firm", please delete "Olsen" and insert --Olson-- therefor.

In Col. 7, line 36, in Claim 13, after "fluid" please insert --flow--.

Signed and Sealed this

Twenty-first Day of November, 2006

JON W. DUDAS
*Director of the United States Patent and Trademark Office*